US012636510B2

(12) United States Patent
Doerr et al.

(10) Patent No.: US 12,636,510 B2
(45) Date of Patent: May 26, 2026

(54) IMPLANTABLE PULSE GENERATOR HAVING A PULSE GENERATION DEVICE

(71) Applicant: BIOTRONIK SE & Co. KG, Berlin (DE)

(72) Inventors: Thomas Doerr, Berlin (DE); Ingo Weiss, Berlin (DE); Juergen Mueller, Zwickau (DE); Thomas Pieske, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 308 days.

(21) Appl. No.: 18/261,872

(22) PCT Filed: Jan. 25, 2022

(86) PCT No.: PCT/EP2022/051582
§ 371 (c)(1),
(2) Date: Jul. 18, 2023

(87) PCT Pub. No.: WO2022/171429
PCT Pub. Date: Aug. 18, 2022

(65) Prior Publication Data
US 2024/0082591 A1　Mar. 14, 2024

(30) Foreign Application Priority Data

Feb. 10, 2021　(EP) ..................................... 21156167

(51) Int. Cl.
*A61N 1/39* (2006.01)
(52) U.S. Cl.
CPC ......... *A61N 1/3956* (2013.01); *A61N 1/3912* (2013.01); *A61N 1/3918* (2013.01);
(Continued)

(58) Field of Classification Search
CPC .. A61N 1/3912; A61N 1/3918; A61N 1/3937; A61N 1/3956; A61N 1/3975;
(Continued)

(56) References Cited

U.S. PATENT DOCUMENTS

| | | | |
|---|---|---|---|
| 5,199,429 A | 4/1993 | Kroll et al. | |
| 2003/0088281 A1* | 5/2003 | Ostroff ................. | A61N 1/3956 607/5 |
| 2016/0101293 A1 | 4/2016 | Ideker et al. | |

FOREIGN PATENT DOCUMENTS

| | | |
|---|---|---|
| EP | 3772361 A1 | 2/2021 |
| WO | 2018026922 A1 | 2/2018 |

OTHER PUBLICATIONS

International Search Report (PCT/ISA/210) with translation and Written Opinion (PCT/ISA/237) mailed on Apr. 13, 2022, by the European Patent Office as the International Searching Authority for International Application No. PCT/EP2022/051582. (13 pages).

* cited by examiner

*Primary Examiner* — Amanda K Hulbert
(74) *Attorney, Agent, or Firm* — Buchanan Ingersoll & Rooney PC

(57) ABSTRACT

An implantable pulse generator comprises a pulse generation device generating an output pulse, the pulse generation device comprising a control unit, shock generation circuitry and output circuitry. The shock generation circuitry comprises a first energy storage device, a second energy storage device and a switching device. The switching device is electrically connected to the first energy storage device, and is configured to connect, in a closed state, the first energy storage device with the second energy storage device, and to disconnect, in an open state, the first energy storage device from the second energy storage device. The shock generation circuitry configured to generate an output pulse by (Continued)

supplying energy to the output circuitry, in the open state, from the first energy storage device via a first connection line and, in the closed state, from the first energy storage device and the second energy storage device via a second connection line.

14 Claims, 4 Drawing Sheets

(52) U.S. Cl.
CPC ......... *A61N 1/3937* (2013.01); *A61N 1/3975* (2013.01); *A61N 1/3987* (2013.01)

(58) Field of Classification Search
CPC .... A61N 1/3987; H02J 7/0024; H02J 7/0025; H02J 7/345; H03K 3/015; H03K 3/57
See application file for complete search history.

IMPLANTABLE PULSE GENERATOR HAVING A PULSE GENERATION DEVICE

CROSS-REFERENCE TO RELATED APPLICATIONS

This application is the United States National Phase under 35 U.S.C. § 371 of PCT International Patent Application No. PCT/EP2022/051582, filed on Jan. 25, 2022, which claims the benefit of European Patent Application No. 21156167.5, filed on Feb. 10, 2021, the disclosures of which are hereby incorporated by reference herein in their entireties.

TECHNICAL FIELD

The instant invention relates to an implantable pulse generator according to the preamble of claim 1 and to a method for operating an implantable pulse generator.

BACKGROUND

An implantable pulse generator of the kind described herein may in particular be an implantable defibrillator, which may be subcutaneously implanted and may comprise one or multiple leads carrying one or multiple electrodes extending from the defibrillator into the patient's heart.

An implantable pulse generator generally comprises a pulse generation device, configured to generate an output pulse, the pulse generation device comprising a control unit, a shock generation circuitry and an output circuitry. The shock generation circuitry comprises at least one first energy storage device, at least one second energy storage device and a first switching device. The control unit is configured to control the shock generation circuitry to generate an output pulse by selectively connecting, using the first switching device, the at least one first energy storage device and the at least one second energy storage device to the output circuitry.

In conventional defibrillators, an arrangement of energy storage devices, for example, in the shape of capacitors, are used to generate an output pulse based on a discharging of the energy storage devices. As a capacitor generally exhibits an exponential decrease in its voltage during discharging, the output pulse conventionally comprises an exponentially decaying waveform.

This leads to the effect that the output pulse, at its beginning, comprises a rather high peak voltage, for example, in excess of 1300 V, making it necessary to use components within the implantable pulse generator which are capable of handling such high voltages.

There hence is a general desire to design an implantable pulse generator such that it may provide for an effective defibrillation, while reducing a peak voltage of the output pulse and hence reducing the requirements for the components of the implantable pulse generator.

International Publication No. WO 2018/026922 A1 discloses an implantable device including one or more leads adapted to be placed in the internal thoracic vein of a patient. The lead may include features to adapt the lead for such placement. An associated device for use with the lead may include operational circuitry adapted for use with a lead having an electrode for sensing and/or therapy purposes coupled thereto.

U.S. Publication No. 2016/0101293 A1 discloses a cardiac defibrillator or cardioversion waveform energy control system employing transvenous ICDs or subcutaneous SICDs for treating cardiac arrhythmias. The system comprises differentially driven amplifier circuit operational modes to control the delivery of defibrillation or cardioversion electrical shocks, wherein the shock waveforms are constant current, constant voltage, or constant energy.

The present disclosure is directed toward overcoming one or more of the above-mentioned problems, though not necessarily limited to embodiments that do.

SUMMARY

It is an object of the instant invention to provide an implantable pulse generator, a method for operating an implantable pulse generator which allow to provide a therapeutically effective shock using a comparatively low shock voltage, and a Method for treating heart failure using a comparatively low shock voltage.

At least this object is achieved by an implantable pulse generator comprising the features of claim 1.

Accordingly, the first switching device is electrically connected, at a first circuit node, to the at least one first energy storage device and is configured to connect, in a closed state, the at least one first energy storage device with the at least one second energy storage device and to disconnect, in an open state, the at least one first energy storage device from the at least one second energy storage device. The shock generation circuitry comprises a first connection line connecting said first circuit node to the output circuitry and a second connection line connecting the at least one second energy storage device to the output circuitry. The shock generation circuitry is configured to generate said output pulse by supplying energy to the output circuitry, in the open state of the first switching device, from the at least one first energy storage device via the first connection line and, in the closed state of the first switching device, from the at least one first energy storage device and the at least one second energy storage device via the second connection line.

The first switching device electrically is placed in between the at least one first energy storage device and the at least one second energy storage device. The first switching device herein serves to electrically connect the at least one first energy storage device to the at least one second energy storage device when the switching device is closed, and to vice versa disconnect the at least one first energy storage device from the at least one second energy storage device when the switching device is opened. In the closed state of the first switching device, hence, the at least one first energy storage device and the at least one second energy storage device are connected in series.

The switching device serves to selectively connect the at least one second energy device to the at least one first energy device in order to supply energy from either only the at least one first energy storage device or from the combination of the at least one first energy storage device and the at least one second energy storage device. In the open state of the switching device, energy is supplied via the first connection line to the output circuitry to generate the output pulse. This in particular may take place in a first time span, causing a discharging of the at least one first energy storage device with a generally exponential decaying waveform. After lapse of the first time span, which, for example, may be preprogrammed or may be set based on a measurement of a charging level of the at least one first energy storage device, to the first switching device may be closed such that the at least one second energy storage device is connected to the at least one first energy storage device, and in a second time span following the first time span energy is supplied to the output circuitry by means of the combination of the at least one first energy storage device and the at least one second energy storage device via the second connection line connected to an output terminal of the at least one second energy storage device opposite the first circuit node.

An output level, in particular an output voltage, for generating the output pulse hence is increased by switching the at least one second energy storage device to the at least one first energy storage device. At the time point of switching the first switching device from the open state to the closed state also the at least one second energy storage device starts to discharge, the output pulse hence again exhibiting an exponentially decaying waveform and an overall toothed shape.

As the at least one second energy storage device may be selectively connected to the at least one first energy storage device in order to generate the output pulse, the output pulse may be shaped such that it exhibits a waveform approximately in the shape of a rectangular pulse. In this way an effective defibrillation may be achieved, while reducing a peak voltage of the output pulse and hence reducing the requirements for components of the pulse generator device. Construction of the pulse generator device hence may be simplified, and costs may be reduced.

Hence, a shock delivery having an approximately rectangular pulse waveform can be achieved by the pulse generator, and in particular a substantially rectangular voltage or current waveform during the pulse delivery may be obtained. In this way, it is possible to deliver a therapeutically effective (defibrillating) pulse over a defined time, while reducing the maximum required shock voltage.

The implantable pulse generator is beneficially suitable for use as a cardioverter defibrillator, using, e.g., therapy voltages of up to 1200 V. Such pulse generator may, for example, be subcutaneously implanted into a patient and, with its housing, may serve as one electrode pole, whereas an electrode placed on a lead extending from the pulse generator may serve as another electrode pole, outside the patient's heart or even outside the patient's thorax.

In one embodiment, the first switching device has the shape of an electronic switch, for example, in the shape of a transistor, such as an IGBT or an AGT or a combination of both.

In one embodiment, the shock generation circuitry comprises a first diode arranged in the first connection line. The first diode in particular serves to assume a conducting state when the first switching device is in its open state and hence energy is delivered via the first connection line towards the output circuitry using only the at least one first energy storage device. Once the first switching device is closed, the first diode assumes a blocking state such that no energy is delivered via the first connection line, but from the combination of the at least one first energy storage device and the at least one second energy storage device via the second connection line.

In one embodiment, the shock generation circuitry comprises a multiplicity of first energy storage devices electrically connected to each other. The first energy storage devices hence, in their combination, form a combined first energy storage device, which in a first time span is used to deliver energy to the output circuitry to generate the output pulse. The first energy storage devices herein are fixedly connected to one another and, for example, are electrically arranged in series or, alternatively, in parallel with respect to one another.

In one embodiment, the shock generation circuitry comprises at least one third energy storage device and a second switching device, wherein the second switching device is electrically connected, at a second circuit node, to the at least one second energy storage device and is configured to connect, in a closed state, the at least one second energy storage device with the at least one third energy storage device and to disconnect, in an open state, the at least one second energy storage device from the at least one third energy storage device. Herein, the second connection line in particular may connect the second circuit node to the output circuitry, the shock generation circuitry comprising a first connection line connecting the at least one third energy storage device to the output circuitry. When the second switching device is opened, the shock generation circuitry generates the output pulse that by supplying energy to the output circuitry from the at least one first energy storage device in combination with the at least one second energy storage device via the second connection line (in the closed state of the first switching device). When in turn the second switching device is closed, the shock generation circuitry generates the output pulse by supplying energy to the output circuitry from the at least one first energy storage device, the at least one second energy storage device and the at least one third energy storage device via the first connection line.

Further energy storage devices may be added to the shock generation circuitry, each arrangement of energy storage devices being connected in series to the arrangement of prior energy storage device by means of an associated switching device, such that by consecutively closing the switching devices more and more energy storage devices may be added for supplying energy to the output circuitry in order to generate the output pulse.

For example, the shock generation circuitry may overall comprise a number in between 2 and 12, for example, 5 or 6, arrangements of energy storage devices connected in series by means of switching devices.

In one embodiment, multiple first energy storage devices are provided, whereas only a single second energy storage device, a single third energy storage device and potentially further single energy storage devices may be provided, a switching device connecting neighboring pairs of the energy storage devices to each other.

In one embodiment, the shock generation circuitry comprises a second diode arranged in the second connection line. If further energy storage devices beyond the (at least one) third energy storage device are provided, further diodes in further connection lines may be provided in order to allow a current flow through a respective connection line in an open state of an associated switching device and to block the current flow in case the switching device is closed.

In one embodiment, one or multiple of the energy storage devices may be formed by capacitors. Alternatively or in addition, one or multiple of the energy storage devices may be formed by inductors. Alternatively or in addition, one or multiple of the energy storage devices may be formed by batteries (primary cells or secondary cells).

For example, capacitors having a single cathode, but multiple anodes may be used.

The energy storage devices may be dimensioned equally with respect to their energy storage capacity, or may be dimensioned differently.

In particular, capacitors forming the different energy storage devices may essentially have identical nominal capacitances (that is, within a tolerance of no more than +/−20%) and/or nominal voltages (that is, within a tolerance of no more than +/−10%) or different capacitances and/or nominal voltages.

In one embodiment, the control unit is configured to control operation of the switching devices. In particular, the control unit is configured to control the first switching device to assume the open state in a first time span and to assume the closed state in a second time span consecutive to the first time span. The control herein may take place in a signal-controlled manner, i.e., based on a measurement, e.g., of a value indicative of a charging level of an energy storage device, in particular a first energy storage device. Alternatively, the control may take place based on a programming, wherein the first time span and the second time span may, for example, be preprogrammed and hence may be initially set.

In one embodiment, the control takes place in a signal-controlled manner based on measurements of a voltage at the first energy storage device. The control may take place such that a deviation of the waveform of the output pulse from an ideal rectangular waveform does not exceed 50%, preferably 20%, i.e., the waveform of the output pulse lies in a range in between +/−50%, preferably +/−20% of the level of the ideal rectangular waveform. The control herein takes place such that a switching device for adding another energy storage device for supplying energy to generate the output pulse is switched from its open state to the closed state prior to a decay of the waveform below an admissible lower bound, for example, below 50%, preferably below to 20% of the ideal rectangular waveform.

Preferably, the control takes place such that teeth formed within the waveform of the output pulse approximately have equal amplitudes, i.e., less than 10% difference between neighboring peaks.

In one embodiment, only the switching of the first switching device in between the at least one first energy storage device and the at least one second energy storage device takes place in a signal-controlled manner, in particular by measuring a voltage associated with the at least one first energy storage device. A switching of further switching devices then takes place in a time-controlled manner based on a length of the first time span after which the first switching device has been switched from its open state to the closed state.

In another embodiment, (also) the switching of the first switching device takes place in a time-controlled manner. For this, the control unit may, for example, be configured to set the first time span based on the following equation:

$$T_1 = R \cdot C \cdot \ln\left(\frac{U_0}{U_e}\right)$$

where $T_1$ is the first time span, R corresponds to a value of a body impedance, C is a capacitance value indicative of a capacitance of the at least one first energy storage device, $U_0$ represents a peak voltage value at the beginning of the first time span, and $U_e$ represents a voltage value at the end of the first time span. The peak voltage at the beginning of the first time span and the voltage at the end of the first time span may be, for example, be modeled and hence are known in advance to set the first time span. The body impedance may be measured, for example, based on a measurement not involving the emission of a shock pulse and hence being substantially unnoticeable (in particular without pain) for a patient, and indicates a coupling of an electrode arrangement to body features of the patient.

Once a switching of the first switching device has taken place, a switching of further switching devices may take place in a time-controlled manner. For example, the control unit may be configured to set the second time span at which the second switching device is switched based on the following equation:

$$T_2 = \frac{N}{N+1} \cdot T_1$$

where $T_2$ indicates the second time span, N indicates the number of first energy storage devices, and $T_1$ indicates the first time span.

A further, $m^{th}$ time for switching a further switching device to add a further energy storage device span may be set based on the following, generalized equation:

$$T_m = \frac{N}{N+m-1} \cdot T_1$$

where $T_m$ indicates a respective further time span, N indicates the number of first energy storage devices, m may assume values between 2 and M+1, with M indicating the number of energy storage devices in addition to the at least one first energy storage device, and $T_1$ indicates the first time span. For this it may be assumed that all capacitors have equal capacitances.

In one embodiment, an overvoltage protection may be established in that, prior to switching, e.g., the first switching device, it is checked whether the output voltage of the at least one first energy storage device has decayed below a predefined threshold, wherein the at least one second energy storage device is connected to the at least one first energy storage device by switching the first switching device if and only if the voltage value is below the threshold. In this way it is avoided that the waveform of the output pulse assumes a voltage, after switching the switching device, above a (non-desirable) upper limit.

In one embodiment, the output circuitry comprises an arrangement of switching devices configured to output, in a first phase, an output pulse of a first polarity and, in a second phase, an output pulse of an inverse, second polarity. Hence, in the first phase, e.g., a positive pulse may be emitted, whereas in the second phase an inverse, negative pulse is emitted. The output circuitry may in particular have the shape of a bridge circuit being formed by an arrangement of switching devices, for example, four switching devices, wherein the switching devices may be selectively switched in order to form different output paths for delivering output pulses of the first polarity or the second polarity.

In one embodiment, the arrangement of switching devices of the output circuitry may be selectively switched in order to interrupt the delivery of output pulses for a predefined time interval. The interruption of the delivery of output pulses can be used to prolong the delivery of therapy. In addition, the interruption of the delivery of output pulses can be used so that the switching of the first switching device or the switching of further switching devices takes place in a time interval where no energy is delivered to tissue.

In one embodiment, all switching devices of the pulse generation device are formed by IGBTs. In another embodiment, the switching devices in series with the energy storage devices are formed by AGTs, wherein the switching devices of the output circuitry at least in part are formed by IGBTs.

According to an embodiment, capacitors forming the energy storage devices are electrolytic capacitors or ceramic capacitors or film capacitors, preferably aluminum or tantalum electrolytic capacitors, preferably having an energy density of at least 4 J*cm³.

In one embodiment, the energy storage devices of the pulse generation device are formed by capacitors having capacitances in the range of 150 μF to 500 μF and/or a nominal voltage in the range of 150 V to 500 V.

The pulse generator device, in one embodiment, is configured to output a therapeutic voltage in the range between 5 to 1000 V, in particular between 5 to 800 V.

The control unit may comprise one or multiple optical couplers (opto-couplers) and/or one or multiple DC/DC drivers for controlling the one or the multiple switching devices of the shock generation circuitry.

At least the object is also achieved by means of a method for operating an implantable pulse generator, comprising: generating, using a pulse generation device, an output pulse, the pulse generation device comprising a control unit, a shock generation circuitry and an output circuitry; controlling, using the control unit, said shock generation circuitry to generate said output pulse by selectively connecting, using a first switching device, at least one first energy storage device and at least one second energy storage device to said output circuitry; and generating, using the shock generation circuitry, said output pulse by supplying energy to the output circuitry, in an open state of the first switching device, from the at least one first energy storage device via a first connection line and, in a closed state of the first switching device, from the at least one first energy storage device and the at least one second energy storage device via a second connection line, wherein the first switching device is electrically connected, at a first circuit node, to the at least one first energy storage device and connects, in the closed state, the at least one first energy storage device with the at least one second energy storage device and disconnects, in the open state, the at least one first energy storage device from the at least one second energy storage device, wherein the first connection line connects said first circuit node to the output circuitry and the second connection line connects the at least one second energy storage device to the output circuitry.

At least the object is also achieved by an implantable subcutaneous cardioverter defibrillator, comprising:

at least a first electrode and at least a second electrode, wherein the first electrode and the second electrode may both positioned outside the heart, and a pulse generation device configured to generate an output pulse.

The pulse generation device comprises a control unit, a shock generation circuitry and an output circuitry. The shock generation circuitry comprises at least one first energy storage device, and the control unit is configured to control said shock generation circuitry to generate said output pulse by supplying energy to the output circuitry. Further the output circuitry is configured to output, in a first phase, an output pulse of a first polarity to deliver a defibrillation shock to said heart using said first electrode and said second electrode, wherein the control unit is configured to control said shock generation circuitry to generate said output pulse of said first phase with a predefined maximum peak voltage of 500-1200 V in such a way, that the voltage of said output pulse during said first phase lies within a range of 0.6 and 1 with respect to said maximum peak voltage.

In one embodiment, the voltage of the output pulse varies over time within the output pulse, wherein the output pulse in the first phase comprises at least one section with a descending voltage and at least one section with an ascending voltage.

In one embodiment, the output pulse in the first phase lasts for at least 2 ms. In a further embodiment, the output pulse in the first phase lasts for at least 3.5 ms.

At least the object is further achieved by a method for treating heart failure, said method involving exposing a human heart to an electrical pulse that is applied to said heart from outside of said heart using an implantable subcutaneous cardioverter defibrillator, comprising at least a first electrode and at least a second electrode and a pulse generation device configured to generate an output pulse. The pulse generation device comprises a control unit, a shock generation circuitry and an output circuitry. The shock generation circuitry is electrically connected to at least one first energy storage device, wherein the control unit is configured to control said shock generation circuitry to generate said output pulse by supplying energy to the output circuitry. The output circuitry is configured to output, in a first phase, an output pulse of a first polarity to deliver a defibrillation shock to said heart using said first electrode and said second electrode and the control unit is further configured to control said shock generation circuitry to generate said output pulse of said first phase with a predefined maximum peak voltage of 500-1200 V in such a way, that the voltage of said output pulse during said first phase lies within a range of 0.6 and 1 with respect to said maximum peak voltage. The output pulse in the first phase lasts for at least 2 ms.

In an embodiment, the output pulse in the first phase lasts for at least 3.5 ms.

At least the advantages and advantageous embodiments described above for the device equally apply also to the method.

Additional features, aspects, objects, advantages, and possible applications of the present to disclosure will become apparent from a study of the exemplary embodiments and examples described below, in combination with the Figures and the appended claims.

BRIEF DESCRIPTION OF THE DRAWINGS

Further features and advantages of the present invention shall be described hereafter based on the description of exemplary embodiments shown in the figures. Herein.

DETAILED DESCRIPTION

Figure 1:
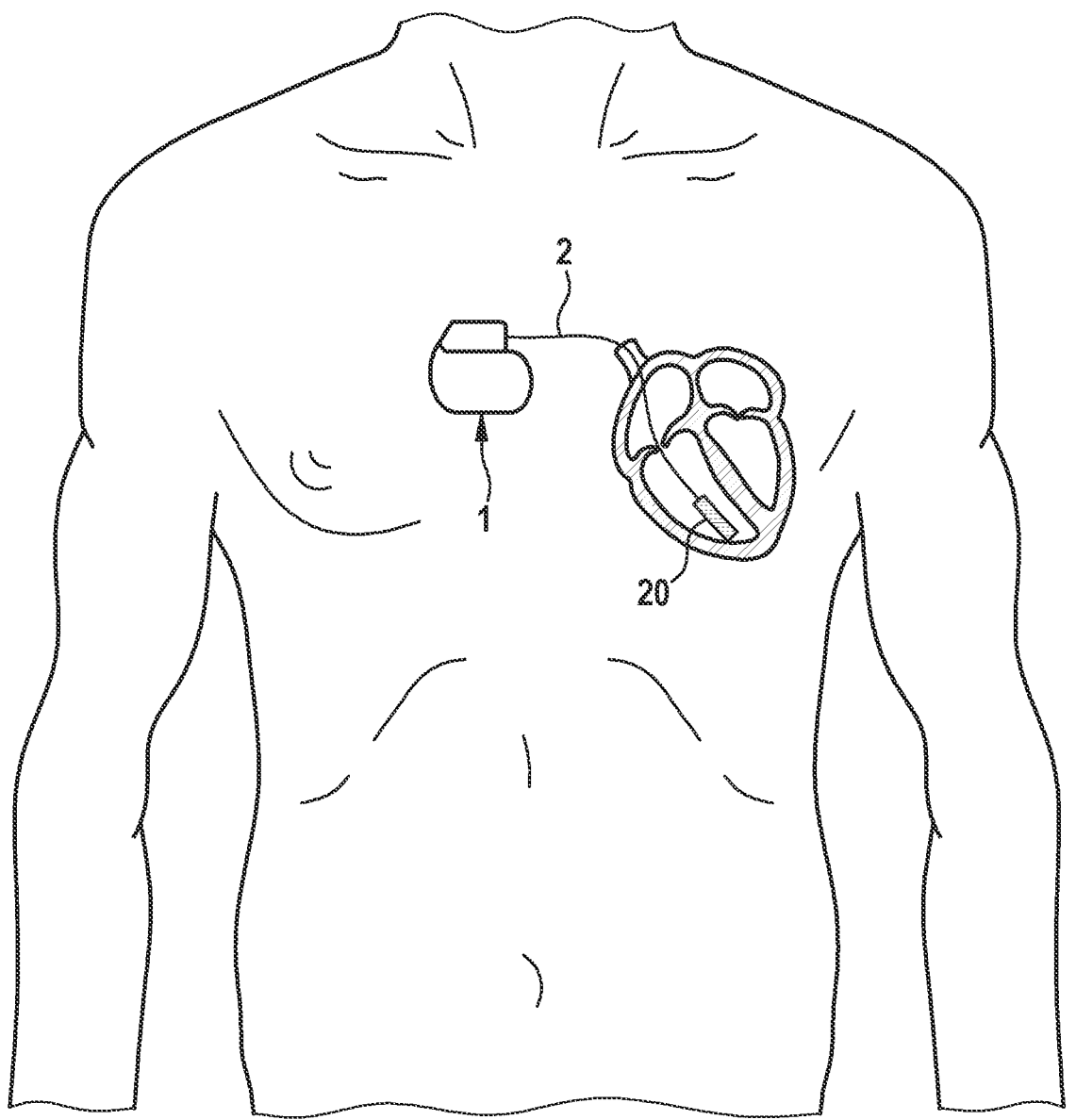
FIG. 1 shows a schematic view of an implantable pulse generator in the shape of an implantable defibrillator.

FIG. 1 shows a schematic view of a pulse generator 1 in an implanted state in a patient. The pulse generator 1 is connected with a lead 2 carrying an electrode 20, the electrode 20 being implanted in a patient's heart such that a defibrillation action may be achieved by injecting a shock pulse into the patient's heart using the electrode 20, with a housing of the pulse generator 1 possibly forming a counter electrode for the electrode 20.

Figure 2:
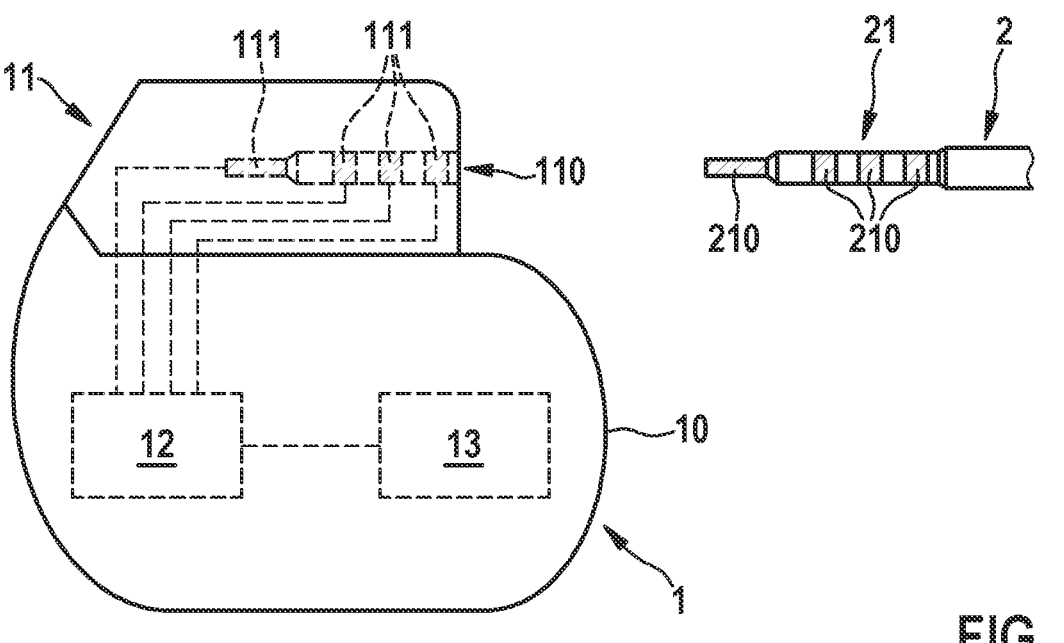
FIG. 2 shows a more detailed schematic view of an implantable pulse generator.

FIG. 2 shows a more detailed view of the pulse generator 1, the pulse generator 1 comprising a housing 10 and a connector block 11 formed on the housing 10, the connector block 11 comprising one or multiple connectors 110 for connecting one or multiple leads 2 by means of connectors 21 to the pulse generator 1. Each connector 110 comprises contact elements 111 for electrically contacting with contact elements 210 of the connector 21 of the lead 2, such that electrical signals may be injected into or received from the lead 2 for causing a therapeutic action or for receiving sense signals in the course of a therapy.

In the embodiment of FIG. 2, the pulse generator 1 comprises a pulse generation device 12 and an energy supply device 13, in particular in the shape of a battery, for supplying electrical energy. The pulse generation device 12 serves to generate shock pulses for injection into a corresponding lead 2 for emitting the shock pulses via an electrode 20 arranged on the lead 2.

Figure 3:
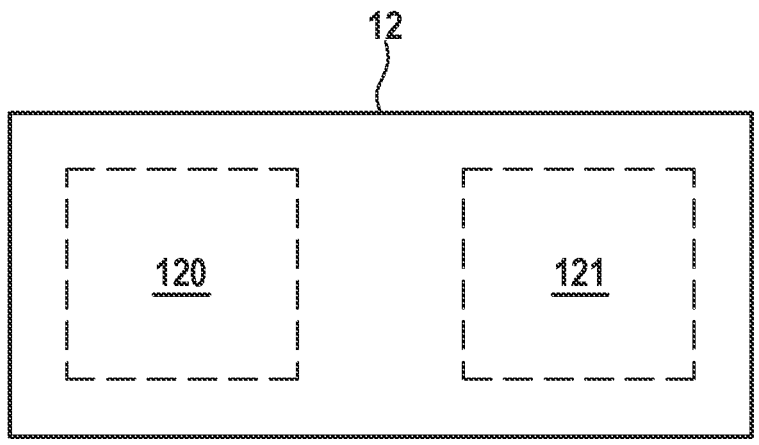
FIG. 3 shows a schematic view of a pulse generation device of an implantable pulse generator.

Referring now to FIG. 3, the pulse generation device 12 comprises a control unit 120 and a shock generation circuitry 121. The pulse generation device 12 in particular, by means of its control unit 120, serves to control action of the pulse generator 1, in particular for generating shock pulses based on a signal analysis of measurement signals sensed in and received from the patient's heart, for example, by means of an electrode arrangement arranged on one or multiple leads connected to the pulse generator 1.

The shock generation circuitry 121 comprises a circuitry for generating an electrical shock pulse. The shock generation circuitry 121 in particular comprises energy storage devices and an output circuitry for generating a high voltage shock pulse and for shaping the shock pulse in a way such that an effective therapeutic (defibrillation) action may be achieved within a patient.

Figure 4:
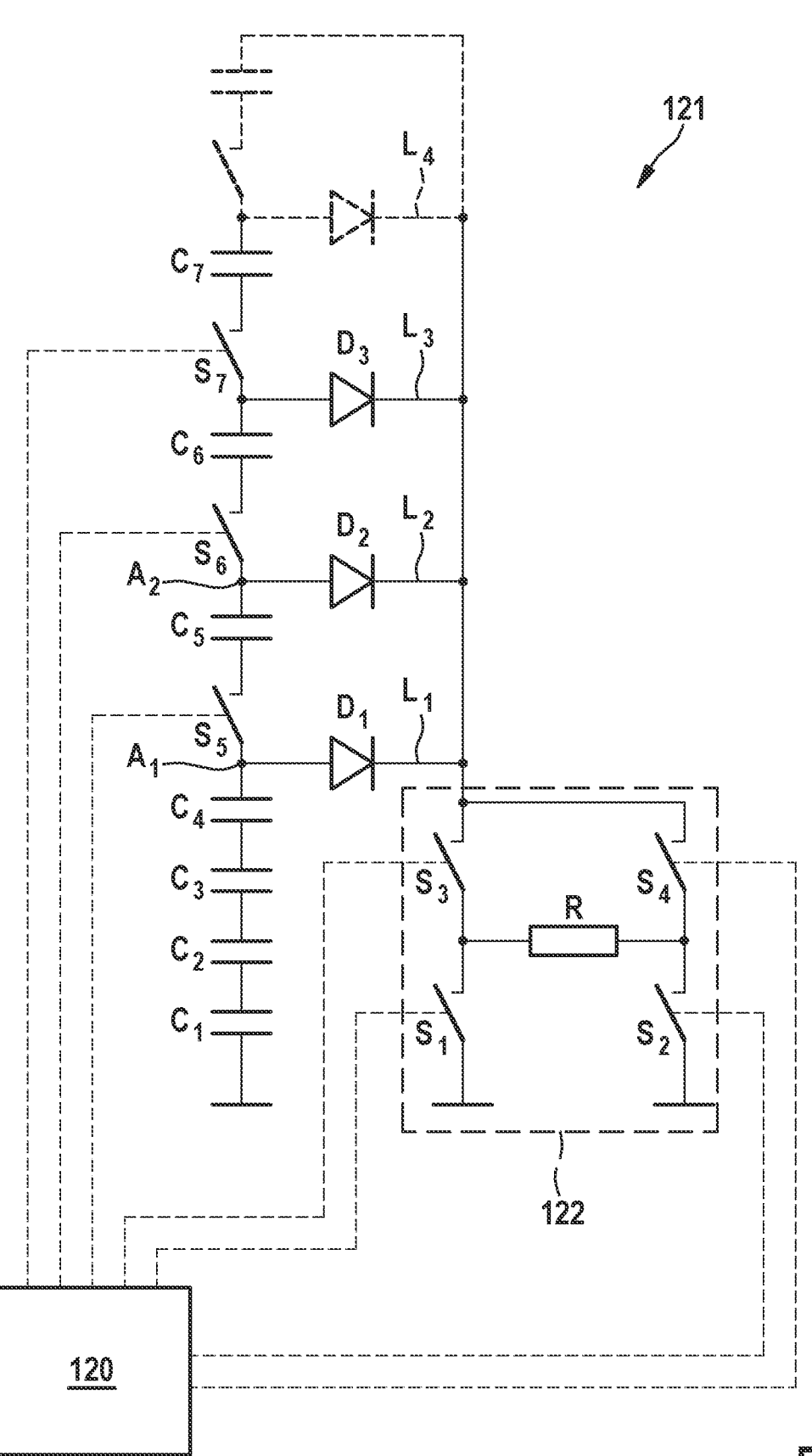
FIG. 4 shows a circuit diagram of a shock generation circuitry of a pulse generation device.

Referring now to FIG. 4, in one embodiment the shock generation circuitry 121 comprises energy storage devices in the shape of capacitors C1 to C7, which each may be charged, for example, by employing a flyback converter with power being supplied from the energy supply device 13 (FIG. 2) in the shape of a battery. The shock generation circuitry 121 in addition comprises switching devices S5 to S7, which serve to selectively couple the energy storage devices C1 to C7 to an output circuitry 122 in the shape of a so-called H bridge, the output circuitry 122 comprising switching devices S1 to S4 for selectively forming a therapeutic current path for injecting a shock pulse into a patient, represented in the schematic circuit diagram of FIG. 4 by an effective body impedance R.

The circuit arrangement of FIG. 4 in particular allows to shape an output pulse such that it may exhibit an approximately rectangular pulse waveform.

In particular, in a first time span when generating an output pulse to achieve a shock therapy, the switching devices S5 to S7 may be in an open state (as illustrated in FIG. 4), such that the arrangement of energy storage devices C1 to C4 (forming first energy storage devices) are connected via a connection line L1 extending from a circuit node A1 to the output circuitry 122, the energy storage devices C1 to C4 being connected in series. During the first time span the energy storage devices C1 to C4 discharge via a diode D1 arranged in the connection line L1 for supplying energy to the output circuitry 122.

In a subsequent, second time span, the switching device S5 is closed, such that the energy storage device C5 (forming a second energy storage device) is connected in series to the energy storage devices C1 to C4, such that energy now is supplied to the output circuitry 122 via a connection line L2 extending from a circuit node A2 at a terminal of the energy storage device C5 opposite to the circuit node A1. Due to the voltage being supplied from the energy storage device C5, the diode D1 in the connection line L1 assumes a blocking state and hence blocks the connection line L1, a diode D2 in the connection line L2 in turn assuming a conducting state such that the energy is supplied via the connection line L2 to the output circuitry 122.

In a third time span the switching device S6 is closed (while the switching device S5 remains closed), such that the further energy storage device C6 (forming a third energy storage device) is connected in series to the other, prior energy storage devices C1 to C5, and energy is supplied to the output circuitry 122 via a connection line L3 connected to a terminal of the energy storage device C6 opposite to the circuit node A2. When the switching devices S5, S6 are closed, the diodes D1, D2 are in a blocking state, such that energy is supplied via the connection line L3 only to the output circuitry 122.

Further energy storage devices C7 beyond the energy storage devices C1 to C6 may be added, which are connected each via an associated switching device S7 in series to the energy devices C1 to C6 below, as illustrated in FIG. 4.

Figure 5:
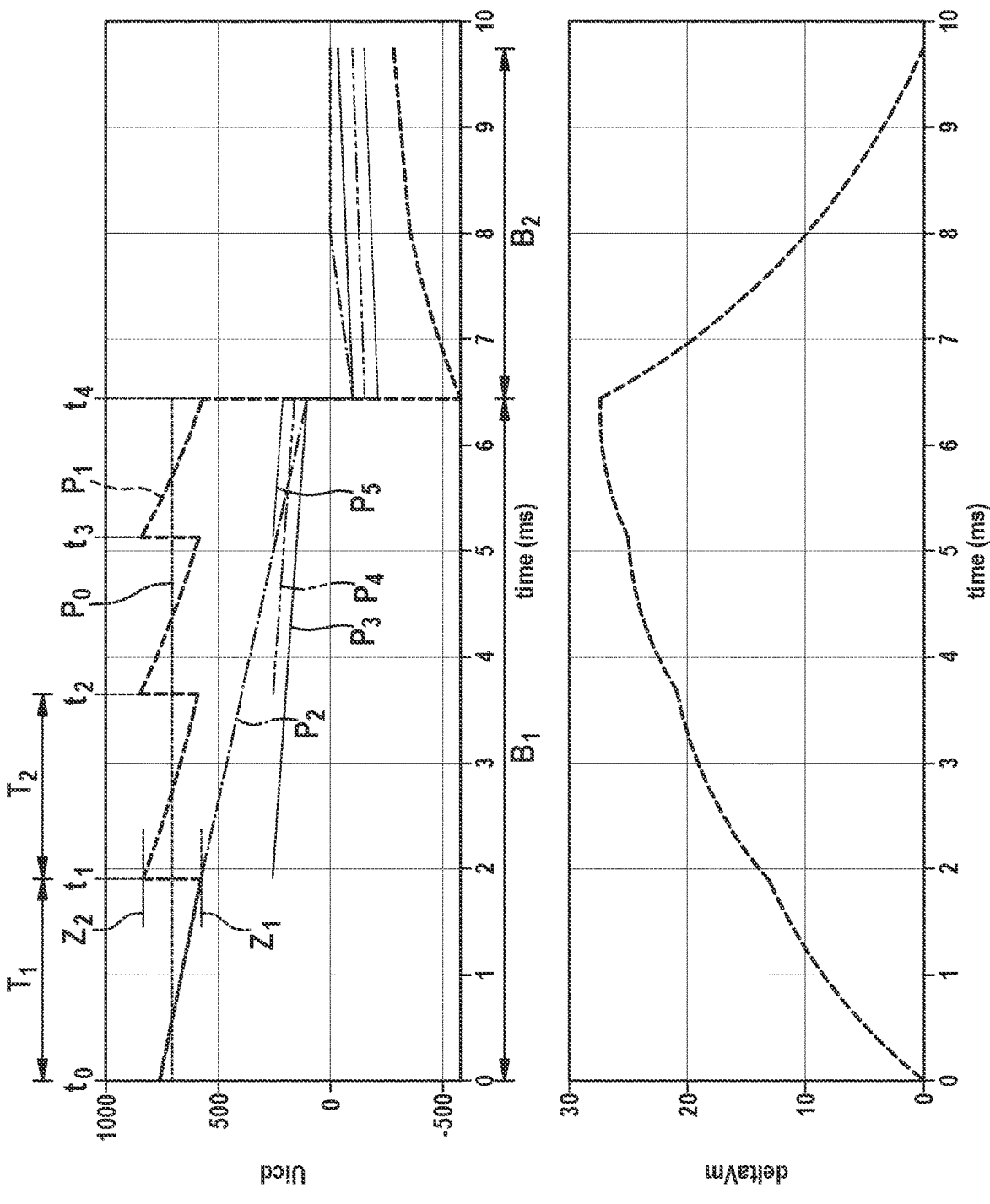
FIG. 5 shows a shock pulse waveform together with an effective defibrillation voltage.

By consecutively adding energy storage devices C1 to C7 for the shaping of the output pulse, the output pulse may assume a waveform P1 which substantially resembles a rectangular waveform P0, as it is shown in FIG. 5 in the graph at the top.

FIG. 5 herein shows discharging waveforms for the arrangement of first energy storage devices C1 to C4 (waveform P2), for the second energy storage device C5 (waveform P3), for the third energy storage device C6 (waveform P4) and for a fourth energy storage device C7 (waveform P5) in addition to the resulting overall waveform P1.

As visible from FIG. 5, in a first phase B1 of a shock pulse the waveform P1 exhibits a toothed shape, due to the consecutive switching of the switching devices S5, S6, S7 for successfully adding energy storage devices when generating an output pulse.

In the first phase B1 herein the output pulse assumes a first polarity, for example, by forming a therapeutic current path in the output circuitry 122 by closing the switching devices S3, S2 and hence injecting a current in a first direction into the body impedance R. In a second phase B2 following the first phase B1, in turn, the polarity of the output pulse is reversed, by now forming a therapeutic current path in the output circuitry 122 by opening the switching devices S2, S3 and by closing the switching devices S4, S1, such that now a current is injected into the body impedance R via a path formed by the switching devices S4, S1.

During the first phase B1, in the example of FIG. 5, the energy storage devices C1 to C7 are successively added, such that the toothed shape of the waveform P1 in the first phase B1 arises. In the second phase B2, in turn, no further energy storage devices are added, such that the waveform P1 in the second phase B2 exhibits a generally (exponentially) decaying shape.

In the first phase B1, following a time point t0 and prior to a time point t1 the switching devices S5 to S7 are open, such that energy is supplied to the output circuitry 122 by the arrangement of first energy storage devices C1 to C4, as indicated in FIG. 4, via the connection line L1 and the diode D1 placed therein.

At the time point t0 the generation of the output pulse starts by suitably switching the shock generation circuitry 121 to the output circuitry 122. At the time point t1, the switching device S5 is closed, such that the energy storage device C5 is connected in series to the energy storage devices C1 to C4, and energy is supplied via the connection line L2 and the diode D2 placed therein.

At a time point t2, the switching device S6 is closed, such that the energy storage device C6 is connected in series to the energy storage devices C1 to C5 below, and energy is supplied via the connection line L3 and the diode D3 placed therein.

At a time point t3, the switching device S7 is closed, such that the energy storage device C7 is connected in series to the energy storage devices C1 to C6 below, and energy is supplied via the connection line L4 to the output circuitry 122.

During each time span, the energy storage devices C1 to C7 respectively connected to the output circuitry 122 are discharged in a generally exponentially decaying manner. At the particular time points t1 to t3, herein a sudden increase in the voltage waveform arises, due to the connection of a respective further energy storage device C5, C6, C7 to the output circuitry 122. Hence, a toothed waveform P1 in the first phase B1 is obtained.

At the time point t4, the polarity of the output pulse is reversed, wherein in the second phase B2 the pulse waveform P1 exhibits a generally exponentially decaying shape.

In FIG. 5 at the bottom a resulting transmembrane voltage of heart muscle cells is shown.

The control of the switching devices S5, S6, S7 may take place in a signal-controlled manner, based on a measurement of a voltage of the arrangement of first energy storage devices C1 to C4, or a measurement of a voltage on all energy storage devices C1 to C7. In particular, the control of the switching devices S5, S6, S7 may be such that the waveform P1 of the output pulse in the first phase B1 lies within a range bounded by a lower bound Z1 and an upper bound Z2, such that the waveform P1 in the first phase B1 approximates the ideal rectangular waveform P0, as illustrated in FIG. 5 in the graph at the top.

In particular, a voltage at the arrangement of first energy storage devices C1 to C4 may be observed, and once it is found that the energy storage devices C1 to C4 have discharged by below a certain value, the switching device S5 may be switched to add the energy storage device C5 and to hence increase the voltage of the output pulse waveform P1 as indicated at the time point t1 in FIG. 5 at the top.

The control of the further switching devices S6, S7 may then take place by measurement of the overall voltage, or based on a time control based on a first time span T1 in between the time points t0 and t1.

For example, the control unit 120 may be configured to set a second time span T2 based on the following equation:

$$T_2 = \frac{N}{N+1} \cdot T_1$$

where $T_2$ indicates the second time span, N indicates the number of first energy storage devices C1-C4, and $T_1$ indicates the first time span.

A further time span for switching a further, $m^{th}$ switching device may then be determined based on the following equation:

$$T_m = \frac{N}{N+m-1} \cdot T_1$$

where $T_m$ indicates a respective further time span, N indicates the number of first energy storage devices C1-C4, m may assume values between 2 and M+1, with M indicating the number of energy storage devices C5-C7 in addition to the first energy storage devices C1-C4, and $T_1$ indicates the first time span.

If the switching of the first switching device S5 does not take place in a signal-controlled manner, but in a time-controlled manner, the control unit 120 may be configured to set the first time spent based on the following equation:

$$T_1 = R \cdot C \cdot \ln\!\left(\frac{U_0}{U_e}\right)$$

where $T_1$ is the first time span, R corresponds to a value of a body impedance, C is a capacitance value indicative of a capacitance of the energy storage devices C1-C7 (assuming that all energy storage devices C1 to C7 have approximately the same capacitance), $U_0$ represents a peak voltage value at the beginning of the first time span T1, and $U_e$ represents a voltage value at the end of the first time span T1, $U_0$ and $U_e$ being known in advance, for example, by suitable electrical modelling).

In the embodiment of FIG. 4, the storage devices C1 to C7 may all comprise equal capacitances, that is a capacitance value within a range of +/−20% around a nominal capacitance. Alternatively, the energy storage devices C1 to C7 may have unequal capacitances.

In the arrangement of FIG. 4, in one embodiment the switching devices S1 to S7 are formed by electronic switches, such as IGBTs or AGTs. In one embodiment, the switching devices S1 to S7 may in part be formed by AGTs and in part by IGBTs. For example, the switching devices S3 to S7 may be formed by AGTs, whereas the switching devices S1 and S2 are formed by IGBTs.

In the arrangement of FIG. 4, in one embodiment the switching devices S1 to S4 of the output circuitry 122 may be selectively switched in order to interrupt the delivery of output pulses for a predefined time interval. For an interruption of the delivery of output pulses at least the switching devices S3 and S4 have to be in an open state. To avoid charge balancing during the interruption of the delivery of output pulses, in addition also one or both of the switching devices S1 and S2 should be in an open state.

The implantable pulse generator 1 may comprise a home monitoring function.

The implantable pulse generator 1 may be MR compatible, when viewed alone and in an implanted state when connected to one or multiple leads 2.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Implantable pulse generator
10 Housing
11 Connector block
110 Connector
111 Contact element
12 Pulse generation device
120 Control unit
121 Shock generation circuitry
122 Output circuitry
13 Energy supply device
2 Electrode lead
20 Electrode
21 Connector
210 Contact elements
A1, A2 Circuit node
B1, B2 Phase
C1-C7 Energy storage device (capacitor)
D1-D3 Diode
L1-L4 Connection line
R Body impedance
P0-P5 Waveform
S1-S7 Switching device
t0-t4 Time point
T1, T2 Time span
Z1, Z2 Bound

What is claimed is:

1. An implantable pulse generator, comprising:
a pulse generation device configured to generate an output pulse, the pulse generation device comprising a control unit, a shock generation circuitry and an output circuitry,
wherein the shock generation circuitry comprises at least one first energy storage device, at least one second energy storage device and a first switching device, and
wherein the control unit is configured to control said shock generation circuitry to generate said output pulse by selectively connecting, using the first switching device, said at least one first energy storage device and said at least one second energy storage device to said output circuitry,
wherein the first switching device is electrically connected, at a first circuit node, to the at least one first energy storage device and is configured to connect, in a closed state, the at least one first energy storage device with the at least one second energy storage device and to disconnect, in an open state, the at least one first energy storage device from the at least one second energy storage device,
wherein the shock generation circuitry comprises a first connection line connecting said first circuit node to the output circuitry and a second connection line connecting the at least one second energy storage device to the output circuitry,
wherein the shock generation circuitry is configured to generate said output pulse by supplying energy to the output circuitry, in the open state of the first switching device, from the at least one first energy storage device via the first connection line and, in the closed state of the first switching device, from the at least one first energy storage device and the at least one second energy storage device via the second connection line,
wherein, in a closed state of the first switching device, the at least one first energy storage device and the at least one second energy storage device are connected in series, and

wherein the shock generation circuitry comprises a first diode arranged in the first connection line.

2. The implantable pulse generator according to claim 1, wherein the shock generation circuitry comprises two or more first energy storage devices electrically connected to each other.

3. The implantable pulse generator according to claim 1, wherein the shock generation circuitry comprises at least one third energy storage device and a second switching device, wherein the second switching device is electrically connected, at a second circuit node, to the at least one second energy storage device and is configured to connect, in a closed state, the at least one second energy storage device with the at least one third energy storage device and to disconnect, in an open state, the at least one second energy storage device from the at least one third energy storage device.

4. The implantable pulse generator according to claim 3, wherein the second connection line connects the second circuit node to the output circuitry, wherein the shock generation circuitry comprises a third connection line connecting the at least one third energy storage device to the output circuitry.

5. The implantable pulse generator according to claim 4, wherein the shock generation circuitry is configured to generate said output pulse by supplying energy to the output circuitry, in the open state of the second switching device, from the at least one first energy storage device and the at least one second energy storage device via the second connection line and, in the closed state of the second switching device, from the at least one first energy storage device, the at least one second energy storage device and the at least one third energy storage device the third connection line.

6. The implantable pulse generator according to claim 1, wherein the shock generation circuitry comprises a second diode arranged in the second connection line.

7. The implantable pulse generator according to claim 1, wherein at least one of the at least one first energy storage device, the at least one second storage device and at least one further third energy storage device is formed by a capacitor or an inductor.

8. The implantable pulse generator according to claim 1, wherein the control unit is configured to control the first switching device to assume the open state in a first time span and to assume the closed state in a second time span subsequent to the first time span.

9. The implantable pulse generator according to claim 8, wherein the control unit is configured to set the first time span based on a programmed value or based on a measurement value indicative of an energy level of the at least one first energy storage device.

10. The implantable pulse generator according to claim 8, wherein the control unit is configured to set the first time span based on the following equation:

$$T_1 = R \cdot C \cdot \ln\left(\frac{U_0}{U_e}\right)$$

where $T_1$ is the first time span, R corresponds to a value of a body impedance, C is a capacitance value indicative of a capacitance of the at least one first energy storage device, $U_0$ represents a peak voltage value at the beginning of the first time span, and $U_e$ represents a voltage value at the end of the first time span.

11. The implantable pulse generator according to claim 8, wherein the control unit is configured to set the second time span based on the following equation:

$$T_2 = \frac{N}{N+1} \cdot T_1$$

where $T_2$ indicates the second time span, N indicates the number of first energy storage devices, and $T_1$ indicates the first time span.

12. The implantable pulse generator according to claim 8, wherein the control unit is configured to set further time spans for generating said output pulse using further energy storage devices based on the following equation:

$$T_m = \frac{N}{N+m-1} \cdot T_1$$

where $T_m$ indicates a respective further time span, N indicates the number of first energy storage devices, m assumes values between 2 and M+1, with M indicating the number of energy storage devices in addition to the at least one first energy storage device, and $T_1$ indicates the first time span.

13. The implantable pulse generator according to claim 1, wherein the output circuitry comprises an arrangement of switching devices configured to output, in a first phase, an output pulse of a first polarity and, in a second phase, an output pulse of an inverse, second polarity.

14. Method for operating an implantable pulse generator, comprising:

16 generating, using a pulse generation device, an output pulse, the pulse generation device comprising a control unit, a shock generation circuitry and an output circuitry, and controlling, using the control unit, said shock generation circuitry to generate said output pulse by selectively connecting, using a first switching device, at least one first energy storage device and at least one second energy storage device to said output circuitry, wherein generating, using the shock generation circuitry, said output pulse by supplying energy to the output circuitry, in an open state of the first switching device, from the at least one first energy storage device via a first connection line and, in a closed state of the first switching device, from the at least one first energy storage device and the at least one second energy storage device via a second connection line, wherein the first switching device is electrically connected, at a first circuit node, to the at least one first energy storage device and connects, in the closed state, the at least one first energy storage device with the at least one second energy storage device and disconnects, in the open state, the at least one first energy storage device from the at least one second energy storage device, wherein the first connection line connects said first circuit node the output circuitry and the second connection line connects the at least one second energy storage device to the output circuitry, wherein, in a closed state of the first switching device, the at least one first energy storage device and the at least one second energy storage device are connected in series, and wherein the shock generation circuitry comprises a first diode arranged in the first connection line.

\* \* \* \* \*